United States Patent [19]

Hevey

[11] Patent Number: 4,863,876

[45] Date of Patent: Sep. 5, 1989

[54] METHOD OF DETECTING AND QUANTIFYING LIGANDS IN LIQUIDS VIA BIOTIN-AVIDIN-MEDICATED FLUORESCENCE POLARIZATION

[76] Inventor: Richard C. Hevey, 881 King Rd., Malvern, Pa. 19355

[21] Appl. No.: 13,581

[22] Filed: Feb. 11, 1987

Related U.S. Application Data

[63] Continuation-in-part of Ser. No. 3,566, Jan. 15, 1987.

[51] Int. Cl.$^4$ ............... G01N 33/566; G01N 33/543; G01N 33/542; G01N 33/533
[52] U.S. Cl. .................... 436/537; 436/501; 436/518; 436/536; 436/541; 436/543; 436/546; 436/800; 436/822
[58] Field of Search ............... 436/501, 518, 536, 537, 436/541, 543, 546, 800, 822

[56] References Cited

U.S. PATENT DOCUMENTS

| | | | |
|---|---|---|---|
| 4,228,237 | 11/1980 | Hevey et al. | 435/7 |
| 4,238,195 | 12/1980 | Boguslaski | 435/7 |
| 4,420,568 | 12/1983 | Wang et al. | 436/536 |
| 4,629,688 | 12/1986 | Boguslaski et al. | 436/537 X |
| 4,640,898 | 2/1987 | Halfman | 436/546 |
| 4,668,640 | 5/1987 | Wang et al. | 436/536 |

FOREIGN PATENT DOCUMENTS 0201211 11/1986 European Pat. Off. .

OTHER PUBLICATIONS

Burd, J. et al., Anal. Biochem., 77: 56–67 (1977).
Williams, E. et al., Anal. Biochem., 155: 249–255 (1986).
D. A. Fuccillo, BioTechniques 3:494–501 (1985).
H. J. Lin & J. P. Kirsch, Analytical Biochemistry, 81:442–446 (1977).
M. H. H. Al-Hakiem et al., Analytical Biochemistry, 166:264 (1981).
J. L. Guesdon et al., J. Histochem. Cytochem. 27:1131–1139 (1979).
I. Hemmila, Clin. Chem. 31:359–370 (1985).

Primary Examiner—Robert J. Warden
Assistant Examiner—Jack Spiegel
Attorney, Agent, or Firm—Hamilton, Brook, Smith & Reynolds

[57] ABSTRACT

A method of determining a ligand of interest in a ligand is described. The method, which makes it possible to detect and quantify a ligand in a liquid, makes use of a biotin-avidin system which can be used to carry out immunoassays in both heterogeneous and homogeneous format. The basic components used in the method are a biotin-labeled substance (which is biotin-labeled ligand or biotin-labeled specific binding partner), biotin-labeled fluorophore, a liquid to be analyzed for the ligand of interest, specific binding partner for the ligand of interest and avidin.

18 Claims, 9 Drawing Sheets

REAGENTS

REACTION

| POLARIZED LIGHT BIOTIN FLUOROPHORE BOUND TO AVIDIN | "FREE" FLUOROPHORE RAPID ROTATION | BIOTIN-ANALYTE BOUND TO AVIDIN BLOCKING AVIDIN BINDING SITES |

Fig. 1

REAGENTS

Ab = ANTIBODY SPECIFIC FOR ANTIGEN (Ag)

Ag = ANTIGEN

Ag▷ = ANTIGEN BOUND BIOTIN

▷–F = BIOTIN BOUND TO FLUOROPHORE (Av) = AVIDIN

REACTION

Ab + Ag + Ag▷ + ▷–F + (Av) ⟶
(3)  (1)   (2)    (4)

ANTIBODY ANTIGEN COMPLEX WITH BIOTIN-ANTIGEN BLOCKED FROM REACTING WITH AVIDIN

ANTIBODY ANTIGEN COMPLEX or

METHOD OF DETECTING AND QUANTIFYING LIGANDS IN LIQUIDS VIA BIOTIN-AVIDIN-MEDICATED FLUORESCENCE POLARIZATION

RELATED APPLICATION

This application is a continuation-in-part of U.S. Ser. No. 07/003,566, filed Jan. 15, 1987, entitled "Method of Detecting and Quantifying Ligands in Liquids", by Richard C. Hevey.

BACKGROUND

Nonisotopic immunoassays are widely used in both clinical and research contexts for the determination of both the presence and quantity of analytes such as proteins, nucleotide sequences, drugs, steroids, etc. Nonisotopic immunoassays can be divided into two types: heterogeneous assays and homogeneous assays.

In heterogeneous assays, a solid support (e.g., beads, a column) is used; some of the labeled reagent becomes bound to the support, while the remainder does not. A procedure is required to separate bound and free labeled reagent.

In homogeneous assays, no separation is required, thus eliminating the need for an additional step. There are at least five major types of homogeneous immunoassays routinely used. Three of these fall into a subcategory of fluorescence immunoassays: substrate-labeled fluorescence immunoassay (SLFIA); Forster energy transfer (FITC) and fluorescence polarization immunoassay (FPIA).

Fluorescence polarization immunoassays can be used to measure small quantities of substances (e.g., in the nanogram-per-milliliter range). They make use of the fact that molecules can exist in a ground or lowest energy state and, after exposure to incident radiation, an excited or higher energy state. Absorption of energy from this source results in promotion of one or more electrons in a molecule to higher energy levels. As this jump occurs, the electron may lose a small percentage of the absorbed energy (e.g., via collisons with other molecules, etc). As its electrons return from higher energy levels to ground state, the excited molecule can radiate energy. The energy generated in this way is, however, less than that originally involved in exciting the molecule. As a result, the wavelength of the light emitted (here, fluorescent light) is longer than that of the light used to excite the molecule. Emitted light energy can be detected using standard equipment, such as a detector positioned at a right angle to the incident light beam. S. Bakerman (ed.), Chem Cues: Fluorescence Polarization Immunoassay, *Laboratory Management*, 16-18 (July 1983); D. Freifelder, Fluorescence Spectroscopy, *In: Physical Biochemistry: Applications to Biochemistry and Molecular Biology* (2d ed.), 537-572 (1982).

An understanding of FPIA also requires an understanding of polarized light. Ordinary light can be thought of as a number of electromagnetic waves, each in a single plane; each wave passes through the central axis or path of the light beam. Polarized light; however, is light in which only one wave plane occurs (the others having been eliminated or screened out). When a fluorescent molecule is oriented such that its dipoles lie in the same plane as the light waves, it absorbs the polarized light. As it returns to its ground state, the molecule emits light in the same plane.

Two additional factors of importance in FPIA are time-related. First, the fluorescence lifetime of the molecule being used must be considered. The lifetime is the interval between excitation of the molecule by a polarized light burst and emission by the molecule of a similar burst. Second, the rotational relaxation time of the molecule—the time necessary for an excited molecule to move out of alignment so that emitted polarized light is emitted in a direction different from its excitation. Small molecules (e.g., haptens) rotate rapidly in solution; their rotational relaxation times are shorter than molecular fluorescence lifetime. As a result, after having absorbed polarized light such small molecules become randomly oriented by the time a burst of polarized emitted light is obtained. Larger molecules (e.g., immunoglobulins) rotate relatively slowly and have rotational times longer than the typical fluorescence lifetime.

Fluorescence polarization measurements rely on the fact that polarized excitation radiation gives rise to polarized emission radiation if no molecular rotation of the fluorophore occurs. A fluorophore is a fluorescent molecule or a compound which has the property of absorbing light at one wavelength and emitting it at a longer wavelength. As described above, the fluorophore bound to a small molecular hapten experiences molecular rotation at a rate that is rapid compared to the lifetime of the excited state prior to emission. Thus, the light is depolarized when bound to a small molecule. When antibody binds the fluorophore-antigen, rotation decreases dramatically because of the large size (molecular weight - 150,000) of the antibody, causing the emitted light to remain polarized.

Immunoassays utilize this phenomenon as follows: with antibody and fluorophore-labeled hapten or antigen present, binding occurs between hapten or antibody and fluorophore-antigen and little fluorescence depolarization occurs. As antigen to be analyzed is added, it binds to antibody competitively, fluorophore antigen is not bound and depolarization is observed. The depolarization is a function of antigen concentration and constitutes a quantitative assay.

Fluorescence polarization has been widely used in the study of the interaction of small (fluorescent) molecules with proteins, (e.g., antibodies). Dandliker, W. B. et al., *Immunochemistry*, 1:165-191 (1964); Dandliker, W. B. and S. A. Levison, *Immunochemistry*, 5:171-183 (1967); Tengerdy, R. P., *Journal of Laboratory and Clinical Medicine*, 70:707-714 (1967). The first applications of the polarization principle in quantitative immunoassays were carried out in 1973 by Dandliker and Spencer et al. Dandliker, W. B. et al., *Immunochemistry*, 10:219-227 (1973); Spencer, R. D. et al., *Clinical Chemistry*, 19:838-844 (1973).

Although the principle of fluorescence polarization immunoassay (FPIA) had been known since the 1970's and feasible instrumentation for the assay with flow-cell and digital read-out has been available since 1973, FPIA has had relatively limited use clinically because it is limited in the size of analytes for whose detection it can be used. The FPIA method is simple, rapid and precise, but its sensitivity is limited. Because only a relatively small change in the polarization occurs, the method is not applicable to antigens whose molecular mass exceeds about 20,000 Daltons.

DISCLOSURE OF THE INVENTION

The present invention relates to a method for determining a ligand in a liquid. Specifically, the invention relates to a method of detecting and quantifying a ligand, which makes use of a biotinavidin system. This system can be used to carry out immunoassays in both heterogeneous format and homogeneous format. It is particularly well suited to determining the presence and the quantity of large molecules (e.g., those having molecular weight of about 20,000 Daltons or more) in a liquid in a homogeneous format. It thus makes it possible to extend the use of fluorescence polarization immunoassay to the detection and quantification of substances (e.g., ligands) of molecular weight above 20,000 Dalton.

According to the method of the present invention, a substance is covalently coupled to biotin to form a biotin-labeled substance; the substance is either a ligand or a specific binding partner for the ligand, resulting in the production of, respectively, a biotin-labeled ligand and a biotin-labeled specific binding partner for the ligand. Biotin is also covalently coupled to a fluorescent material (biotin-labeled fluorophore).

The basic components used in the method of the present invention are: (1) a biotin-labeled substance; (2) a biotin-labeled fluorophore; (3) a liquid or sample (containing the ligand whose presence and/or quantity are to be determined—the ligand of interest); (4) specific binding partner for the ligand of interest; and (5) avidin.

In one embodiment of the method of the invention, immunoassay is carried out in homogeneous format. That is, one method for determining the presence and quantity of a ligand in a liquid according to the present invention is as follows: A known volume of liquid to be analyzed for the ligand of interest is incubated (combined) with a known quantity of the ligand of interest which is labeled with biotin; a quantity of specific binding partner for the ligand of interest; a biotin-labeled fluorophore; and avidin. The resulting combination is maintained under conditions appropriate for specific binding reactions (reaction between the ligand and its specific binding partner) to occur. Fluorescence polarization is determined using known techniques, before and after the addition of avidin. The difference in fluorescence polarization (e.g., with and without avidin present) can be done sequentially or simultaneously. That is, a known quantity of avidin is added, either along with the other components or after the other components have been combined and specific binding reactions have occurred. In the first case, the change in fluorescence polarization is measured simultaneously; in the latter, it is measured sequentially. The change serves as an indication of the presence and quantity of ligand in the liquid. It is also possible to compare the fluorescence polarization of the combination with that of an avidin-free control. Background fluorescence polarization (that is caused by the components themselves) can be determined and subtracted, as described below, to increase the sensitivity of the assay.

A method of the present invention which can also be used in a homogeneous format makes use of a biotin-labeled fluorophore, a liquid to be analyzed for a ligand of interest, a specific binding partner for the ligand, ligand bound to biotin, and avidin. In this method of determining the presence and quantity of a ligand in a liquid, the biotin-bound ligand is pre-reacted with its specific binding partner or with avidin. In the first case, the resulting complex (biotin-bound ligand/specific binding partner or biotin-bound ligand/avidin), a biotin-labeled fluorophore and avidin are added to a known volume of liquid to be analyzed for the ligand of interest. In the second case, the resulting complex (biotin-bound ligand/avidin), a biotinlabeled fluorphore and a specific binding partner are added to a known volume of liquid to be analyzed for the ligand of interest. The change in fluorescence polarization (before and after addition of avidin or ligand) is measured and serves as an indicator of the presence and quantity of the ligand of interest. Alternatively, the fluorescence polarization of the combination can be compared with that of an avidin-free control.

In another embodiment of the method, an insoluble phase containing a specific binding partner for the ligand of interest is used. This embodiment is useful in the determination of ligands which have one or more binding points or sites for their specific binding partners. The components of the system are incubated (combined) under conditions appropriate for specific binding reactions to occur (e.g., between ligand and its specific binding partner). Following the specific binding reactions, the fluorescent polarization of the soluble phase is determined.

Specifically, the presence and quantity of a ligand in a liquid are determined as follows: An insoluble phase containing a specific binding partner for the ligand is incubated with a known volume of liquid to be analyzed for the ligand of interest and biotin-labeled ligand. Unreacted reagents (which are in the soluble phase) are separated from the insoluble phase after incubation and fluorescence polarization of the soluble phase is measured. A biotin-labeled fluorophore and a known quantity of avidin are then added to the soluble phase. Fluorescence polarization is again measured using known techniques. The change in fluorescence polarization is determined and serves as an indication of the presence and quantity of ligand in the liquid. Alternatively, fluorescence polarization of the incubated combination can be compared with that of an avidin-free control.

In another embodiment, an insoluble phase containing a specific binding partner for the ligand of interest is reacted with a ligand which has at least two binding points or sites for its specific binding partner. Biotin-labeled binding substance and avidin are added. The components are combined under conditions appropriate for specific binding reactions to occur (e.g., between ligand and its specific binding partner) and for biotin and avidin to bind. The soluble phase is separated from the insoluble phase and an aliquot of uncoupled avidin (e.g., of the soluble phase) is removed and reacted with a biotin-labeled fluorophore. After specific binding reactions have occurred, the fluorescent polarization of the soluble phase is determined.

An alternative embodiment of the present invention which can be used to determine the presence and quantity of a ligand which has more than one binding point or site for the specific binding partner involves use of an insoluble phase containing a specific binding partner for the ligand of interest. In this embodiment, the insoluble phase is incubated with a known quantity of liquid to be analyzed for the ligand of interest and biotin-labeled specific binding partner for the ligand (which is bound to the solid phase specific binding partner). Incubation is carried out under conditions appropriate for specific binding reactions to occur. Unreacted reagents are separated from the insoluble phase and a known quantity of avidin is added to the insoluble phase. Fluorescence polarization of the insoluble phase is determined using known techniques. Unreacted reagents are again separated from the insoluble phase and a biotin-labeled fluorophore is added either to the insoluble phase or to the separated liquid phase. Fluorescence polarization due to binding of biotin-labeled fluorescent material, either to the avidin on the insoluble phase or to unreacted avidin in the liquid phase, is determined. The change in fluorescence polarization is determined and serves as an indication of the presence and quantity of ligand in the liquid.

The method of the present invention can also be used for the determination of DNA. Its use in determining the presence and quantity of DNA in a liquid can be briefly described as follows:

A known volume of liquid containing DNA of interest is placed upon a nitrocellulose solid phase (e.g., nitrocellulose filter). Biotin-labeled DNA having a nucleotide sequence complementary to the DNA of interest is added to the nitrocellulose solid phase. Bound and free biotin-labeled DNA are separated and reacted with avidin and biotin-labeled fluorophore. The degree of fluorescence polarization caused by binding of the biotin-fluorophore to avidin is determined using known techniques.

The ligand determination performed according to the method of the present invention can be accomplished through use of either a noncompetitive binding reaction or a competitive binding reaction.

The method of the present invention makes it possible to accurately determine the presence and quantity of a ligand of interest in a liquid quickly, without use of radioactive reagents.

DETAILED DESCRIPTION OF THE INVENTION

The method of determining a ligand of interest in a liquid through the measurement of fluorescence polarization which is the subject of the present invention makes use of the high binding effect between biotin and avidin. The method of the present invention can be used in both homogeneous binding processes and heterogeneous binding processes; however, competitive homogeneous or non-competitive homogeneous binding processes are preferred.

Determination of the presence and quantity of a ligand of interest in a liquid is carried out through use of a biotin fluorescent polarization detection system. Use of this system takes advantage of the high binding affinity of avidin for biotin as a means of detecting and quantitating biotin or biotin-bound ligand. It is also possible to use anti-biotin antibody in place of avidin; for example, a monoclonal anti-biotin antibody can be used.

The basic components used in the method of the present invention are: (1) a biotin-labeled reagent, which is generally a biotin-labeled ligand, but can also be a biotin-labeled specific binding partner; (2) a biotin-labeled fluorophore; (3) a liquid or sample to be analyzed for a ligand of interest; (4) a specific binding partner for the ligand of interest; and (5) avidin.

Generally, these components are combined at one time or in a selected sequence; the determining consideration in which procedure is used is the ability of the selected approach to result in binding of avidin to biotin in the desired manner (e.g., one which allows measurement of fluorescence polarization and its use as an indicator of the presence and/or quantity of the ligand of interest in the liquid).

As mentioned, the method of the present invention can be used in both homogeneous binding processes or immunoassays (i.e., those which do not require separation of bound and free fractions of the labeled reagent) and heterogeneous binding processes or immunoassays (i.e., those which require a distinct step to separate the two reagent fractions).

Figure 1:
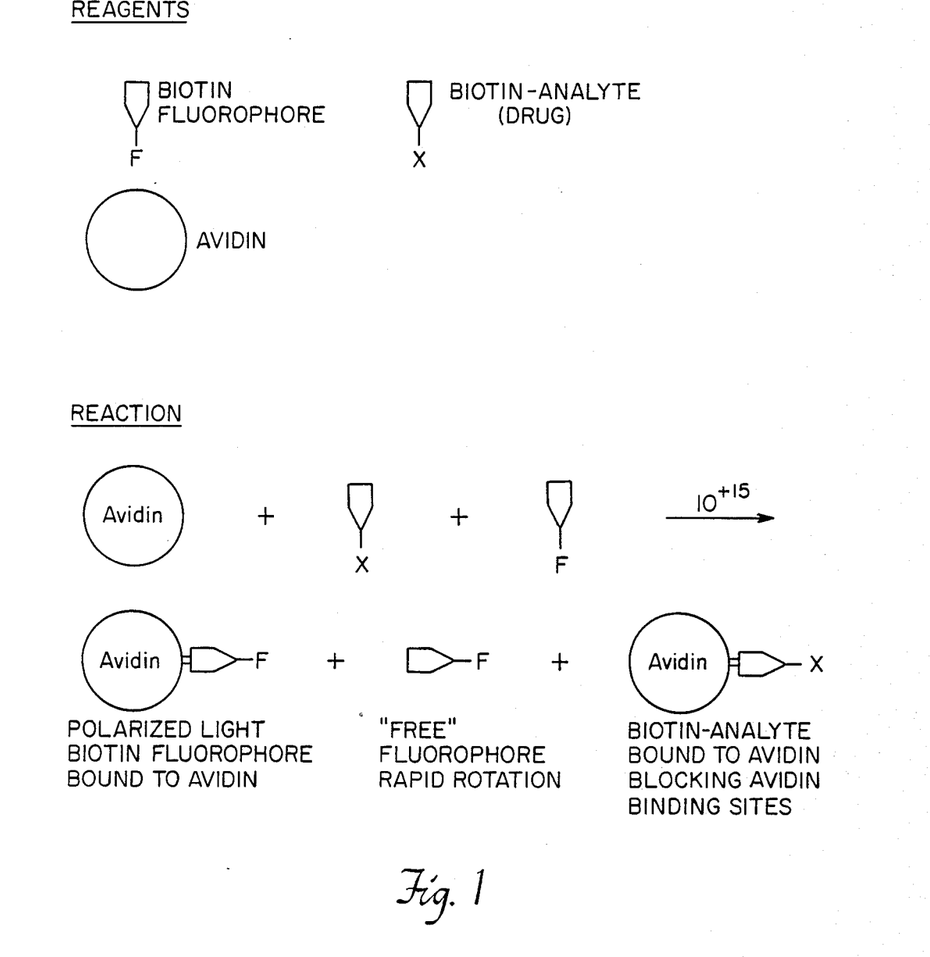
FIG. 1 is a schematic representation of the reactions occurring when biotin-labeled fluorophore, biotin-labeled ligand and avidin are combined and of the effect on fluorescence polarization.

FIG. 1 is a schematic representation of reactions which occur among biotin-labeled ligand or analyte, biotin-labeled fluorophore and avidin when they are combined. A fluorophore is a fluorescent material and has the property of absorbing light at one wavelength and emitting it at another (longer) wavelength. As shown, avidin binds to biotin-labeled ligand, blocking avidin binding sites otherwise available for binding to biotin-labeled fluorophore. Avidin also binds with biotin-labeled fluorophore, resulting in fluorescent complex. Finally, some biotin-labeled fluorophore remains unbound (free) and undergoes rapid rotation.

Figure 2:
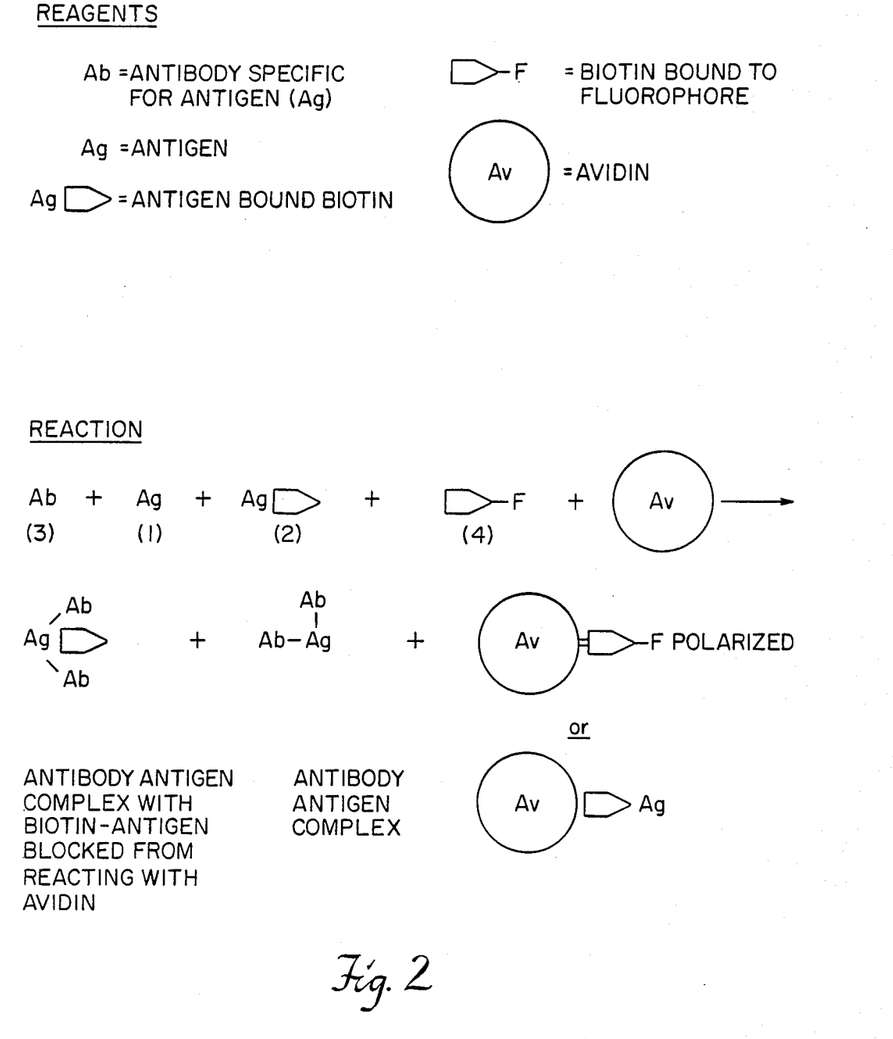
FIG. 2 is a schematic representation of an immunoassay carried out in homogeneous format according to the method of the present invention.

An example of the use of the method of the present invention in homogeneous immunoassays is represented in FIG. 2. As shown, the following components are used: (1) a biotin-labeled ligand (here, a biotin-labeled antigen); (2) a biotin-labeled fluorophore; (3) an unknown quantity of a ligand of interest (here, an antigen) present in a liquid sample of known volume; (4) a specific binding partner for the ligand of interest (here, antibody specific for antigen); and (5) avidin.

In this case, the following are incubated (combined) under conditions appropriate for specific binding reactions (i.e., reactions between ligand (antigen) and its specific binding partner (antibody)) to occur: (1) a known quantity of liquid to be analyzed for the ligand (antigen) of interest; (2) a known quantity of biotin-labeled ligand (antigen); (3) a known quantity of specific binding partner (antibody); (4) biotin-labeled fluorophore; and (5) a quantity of avidin. Components 1–4 can be combined simultaneously or sequentially. For greater sensitivity, it is also possible to combine the components sequentially and to vary the order in which the components are combined. For example, it is possible to combine biotin-labeled ligand, an unknown quantity of a ligand of interest (in a known volume of liquid) and a specific binding partner and to incubate them. Avidin is added, followed by a biotin-labeled fluorophore. The components can also be combined sequentially in the following order: biotin-labeled ligand; an unknown quantity of ligand (in a known volume of liquid); specific binding partner for the ligand of interest; biotin-labeled fluorophore; and avidin.

Fluorescence polarization can be measured, using known techniques, before and after the addition of avidin. Alternatively, fluorescence polarization can be measured after all five components have been combined and the resulting measurement compared with that for an avidin-free control (i.e., which includes components 1–4 listed above). An increase in polarization when avidin is present is indicative of its binding to the biotin-labeled fluorophore. The extent of increase in polarization is inversely related to the quantity of the ligand of interest present in the liquid analyzed. For example, as the quantity of antigen present in the liquid to be analyzed decreases, biotin-antigen binding with antibody increases. The biotin in the biotin-antigen-antibody complex is not available to react with added avidin. Thus, more binding of the biotin-fluorophore to avidin occurs than is the case when a large quantity of antigen is present in the liquid. As a result, much of the biotin-labeled fluorophore binds to avidin; the avidin-biotin fluorophore is fluorescent and polarization is greater than is the case when a large quantity of antigen is present. The amount of ligand of interest in a liquid can be determined by comparing the fluorescence polarization of the liquid with that of a standard of known concentration. For example, it can be compared with a standard curve prepared by measuring the fluorescence polarization of liquids of varying known avidin concentrations. Alternatively, it can be determined by comparing the fluorescence polarization of the liquid with that of a standard liquid whose fluorescence polarization is also read.

It is also possible to substract background fluorescence, and thus increase the assay's sensitivity. To subtract background fluorescence due to the presence of the components themselves, the following steps are carried out: (1) a known quantity of liquid to be analyzed for the ligand of interest, a known quantity of biotin-labeled ligand, a known quantity of specific binding partner and avidin are combined; (2) fluorescence polarization of the combination is measured. This results in a measurement of the fluorescence polarization of the sample itself. Comparison with an avidin-free control, as described above, results in determination of the quantity of ligand of interest present in the sample. The background fluorescence of the avidin-free control can also be subtracted or removed by combining components 1, 2 and 3 listed above, measuring fluorescence, adding component 4, again measuring fluorescence and determining the difference between the two measurements. Then fluorescence polarization of the avidin-free combination is determined; this provides measurement of fluorescence polarization of the control.

If a homogeneous immunoassay is to be carried out for a ligand of interest which is an antibody, the procedure is similar to that described above for determination of an antigen. Such an assay is useful for determining antibodies of interest such as anti-rubella antibodies, anti-DNA antibodies and anti-insulin antibodies. Here, however, a known quantity of liquid to be analyzed for an antibody of interest is incubated with a known quantity of biotin-labeled specific binding partner (which in this case is biotin-labeled antigen, such as biotin-labeled virus or insulin), biotin-labeled fluorophore and avidin. The components can be combined simultaneously or sequentially and, as described above, the order in which they are combined can be varied (e.g., to increase sensitivity).

As also described above in the description of antigen assay, fluorescence polarization can be measured before and after the addition of avidin, to produce a measurement of the change in fluorescence polarization. Alternatively, it can be determined after avidin is added and compared with the fluorescence polarization of an avidin-free control. Here, too, background fluorescence of the sample can be subtracted, thus increasing the assay's sensitivity.

Use of the method of the present invention in homogeneous binding processes may be varied in that biotin-labeled ligand (e.g., biotin-labeled antigen) may be pre-reacted with its specific binding partner (antibody) to form a biotin-labeled ligand/specific binding partner (biotin-labeled antigen/antibody) complex. The resulting complex is incubated with a biotin-labeled fluorophore, a liquid sample of known volume containing an unknown quantity of a ligand of interest and avidin. As described above, fluorescence polarization is measured before and after the addition of avidin and the change determined. The extent of fluorescence polarization varies inversely with the quantity of antigen present in the sample; that is, as the quantity of antigen increases, polarization decreases.

In another embodiment, biotin-labeled specific binding partner is pre-reacted with avidin to produce a biotin-labeled specific binding partner/avidin. The resulting complex is incubated with a known volume of liquid sample having an unknown quantity of ligand. Biotin-labeled fluorophore is added and fluorescence polarization is determined. The amount of polarization is compared with that of a control which does not contain avidin.

Figure 3:
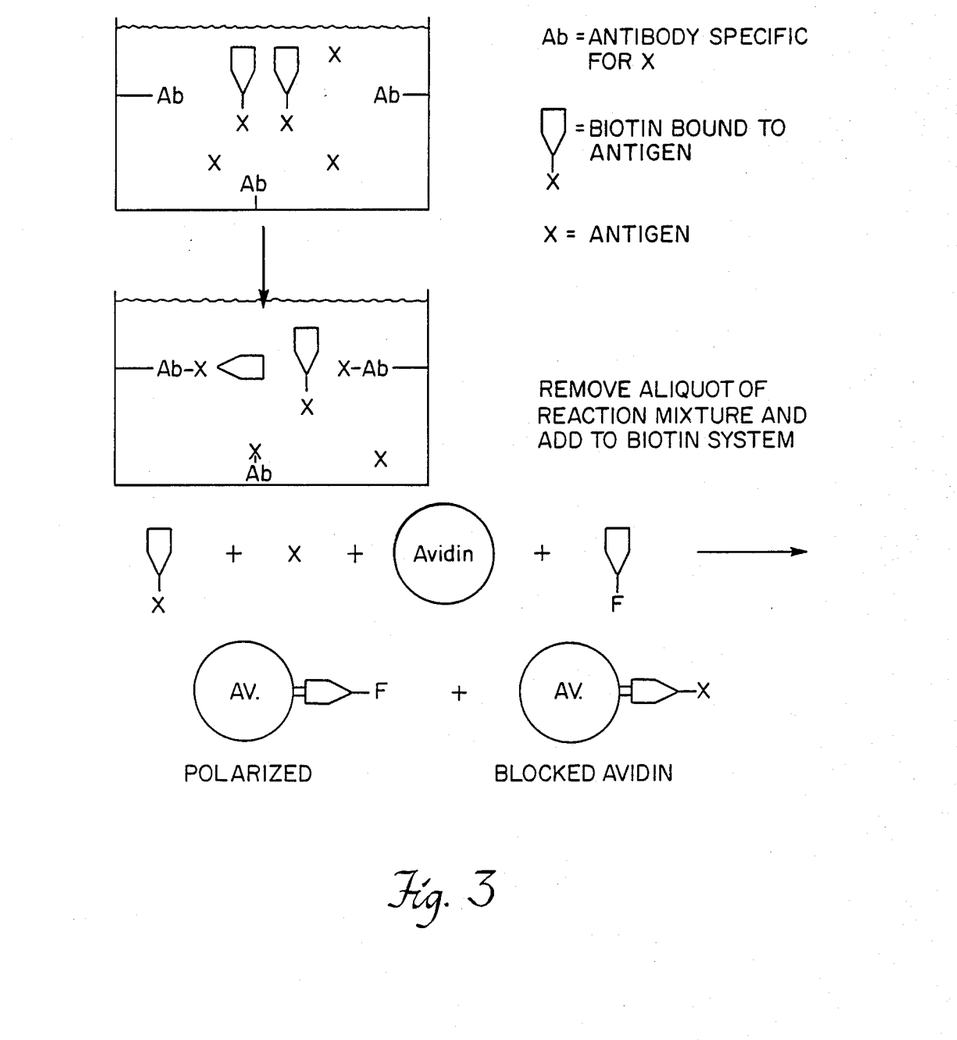
FIG. 3 is a schematic representation of an immunoassay carried out in heterogeneous format according to the method of the present invention.

An example of the use of the method of the present invention in heterogeneous immunoassays is represented in FIG. 3. As represented, the components used are: (1) a biotin-labeled reagent (here, a biotin-labeled antigen); (2) a biotin-labeled fluorophore; (3) an unknown quantity of a ligand of interest (here, an antigen) in a known volume of ligand; (4) a specific binding partner bound to a solid phase (here, antibody specific for antigen); and (5) avidin. In this case, a known quantity of liquid to be analyzed for the ligand (antigen) of interest, biotin-labeled ligand and an insoluble phase containing a specific binding partner (antibody) for the ligand are incubated (combined) under conditions appropriate for specific binding reactions to occur. After incubation, the insoluble phase and the soluble phase of the reaction mixture are separated. A known volume of the soluble phase is incubated with a biotin-labeled fluorophore and a known quantity of avidin, as illustrated in the lower portion of FIG. 3. Fluorescence polarization is measured, using known techniques, before and after the addition of avidin. Alternatively, fluorescence polarization of the final combination can be measured (after incubation) and compared with fluorescence polarization of an avidin-free control. An increase in polarization when avidin is present is indicative of its binding to the biotin-labeled fluorophore. The extent of increase in polarization is indirectly related to the quantity of the ligand of interest present in the liquid analyzed. Fluorescence polarization measurements are compared with a standard (e.g., representing fluorescence polarization of solutions of known concentrations) to determine the quantity of ligand of interest present.

Here, too, it is possible to subtract background fluorescence and thus increase the assay's sensitivity. This is done in the following manner: A known quantity of liquid to be analyzed for the ligand of interest, biotin-labeled ligand and an insoluble phase containing a specific binding partner for the ligand are incubated (combined) under conditions appropriate for specific binding reactions to occur. The insoluble phase and the soluble phase are then separated. A known volume of the soluble phase is combined with avidin and fluorescence is measured. Biotin-labeled fluorophore is subsequently added and fluorescence is again measured. The determination of fluorescence polarization can thus be obtained with background subtracted. An alternative approach to using the method of the present invention in heterogeneous binding processes is possible if the ligand to be detected in liquid has more than one point or site at which it can bind to a specific binding partner. In this case, an insoluble phase containing a specific binding partner (e.g., antibody) for the ligand (e.g., antigen) to be detected is incubated either sequentially or simultaneously, with a known volume of the liquid to be analyzed and biotin-labeled specific binding partner for the ligand bound to the solid phase specific binding partner. The soluble (liquid) phase (unreacted reagents) and the insoluble phase are separated and a known quantity of avidin is incubated with the insoluble phase. The soluble phase (unreacted avidin) and the insoluble phase (bound avidin) are separated and a biotin-labeled fluorophore is incubated with either the unreacted avidin in the soluble phase or the avidin on the insoluble phase. Fluorescence polarization is measured, using known techniques, before and after the last incubation (with biotin labeled fluorophore). An increase in polarization is due to binding of the biotin-labeled fluorophore to either the avidin bound to the insoluble phase or the unreacted avidin in the soluble phase. In the first case, in which avidin bound to the solid phase is being measured, fluorescence polarization is directly related to the amount of ligand of interest (e.g., antigen) present in the sample; fluorescence polarization increases as ligand increases. In the second case, in which free avidin is being measured, fluorescence polarization is inversely related to the quantity of ligand present; fluorescence polarization decreases as ligand concentration increases. In addition, the soluble phase of the first incubation can be reacted with avidin and biotin-fluorophore sequentially.

In the case of competitive binding reactions, biotin-bound ligand and a biotin-labeled fluorescent compound (fluorophore) compete for binding to avidin. As the concentration of biotin-bound ligand increases, binding of the biotin-labeled fluorescent compound decreases; that is, if the concentration of biotin-bound ligand is high, binding of biotin-fluorophore to avidin is less than if the concentration of biotin-bound ligand is low. According to the theory of fluorescence polarization, binding of biotin-fluorophore to avidin results in an increase in polarization; the intensity of polarization is related to the concentration of biotin-fluorophore bound to avidin.

In the case of non-competitive binding reactions, sequential addition of materials (e.g., biotin labeled ligand or fluorophore, ligand, avidin) can be employed to yield as sensitive assay as with the competitive approach.

Ligands which may be determined according to the present invention are compounds for which one or more specific binding partners can be provided. Such a specific binding partner is any substance or group of substances which has a specific binding affinity for the ligand, to the exclusion of other substances. Ligands which may be determined through the method of the present invention include, for example, antigens, antibodies, haptens (drugs or other small organic molecules), nucleic acid sequences (e.g., DNA, RNA) and other substances which have naturally occurring receptors.

When the ligand is an antigen, the specific binding partner used to detect the antigen is normally the corresponding antibody produced when the antigen is introduced into the blood stream of a vertebrate. Examples of antigens which may be determined according to the instant invention include, for example, polypeptide and protein hormones, human IgE and alpha fetoprotein, a fetal antigen that also occurs in serum of patients with hepatoma and embryonal adenocarcinoma. When the ligand is an antibody, the eliciting antigen may be employed as a specific binding partner. Assay of antibody titers is particularly useful in the diagnosis of, for example, infectious diseases such a syphillus, rubella and infection caused by haemolytic streptococci.

When the ligand is a hapten (i.e., a proteinfree substance which does not itself elicit antibody formation), specific binding partner utilized to detect the hapten is an antibody produced when the hapten, bound to an antigenic carrier, is introduced into the bloodstream of a vertebrate. Examples of haptens which may be determined according to the instant invention include steroids such as estrone, estradiol, testosterone, pregnanediol and progesterone; vitamins such as $B_{12}$ and folic acid; triodothyronine, thyroxine, histamine, serotonine, digoxin, prostaglandins, adrenalin, noradrenalin, morphine, hormones, and antibiotics, such as penicillin.

When the ligand is a substance having a naturally occurring receptor, the receptor can be utilized as the specific binding partner for detecting the ligand, if the receptor can be isolated in a form specific for the ligand. Ligands which have naturally occurring receptors include, for example, thyroxine, many steroids, polypeptides, such as insulin and angiotensin and many others. Receptors for this class of ligands are usually proteins or nucleic acids.

Ligands which are determined according to the instant invention with the aid of a non-competitive binding process (i.e., the "Sandwich" technique) must have at least two points or sites for binding to their specific binding partner in order to bind with both the insoluble phase containing specific binding partner and biotin labeled specific binding partner. This is not necessary when a competitive binding process is employed.

Preparation of the biotin labeled substance (i.e., biotin-labeled specific binding partner or biotin-labeled ligand) may be accomplished by simply mixing the entity to be labeled with biotin N-hydroxysuccinimide ester (BNHS) in a suitable solvent such as dimethylformamide. Although the use of BNHS is preferred, other suitable reagents and/or methods may be employed.

Biotin-labeled fluorescent compound (fluorophore) can be any fluorescent compound, labeled with biotin, which exhibits polarization. For example, fluorescein, rhodamines, pyrine-derivatives, umbellipherones and porphyrins can be used. Biotin-fluorescein is particularly useful in the method of the present invention and can be prepared in the following manner: Fluorescein isothiocyanate, 10 mg (25 umoles), is dissolved in 2 mls of dimethylformamide; 8 ul of ethylene diamine (120 umoles) are added at room temperature. The precipitate formed is recrystallized in dimethylformamide, filter and dried. (The precipitate may form immediately; however, the reaction is allowed to proceed for 40 hours.) The fluorescein-ethylene diamine adduct, 6.5 mg (14 umoles) is dissolved in 2 mls of dimethylsufoxide; 9 mg (26 umoles) of N-hydroxysuccinimidobiotin are added and the resulting mixture allowed to stand at room temperature for several hours. The conjugate is purified by chromatographing 100 ul of the above reaction mixture on a silica gel column (2×1.5 cm, 230–400 mesh, 60A pore size), preequilibrated and eluted with methanol.

Preparation of the insoluble phase containing specific binding partner for the ligand to be determined can be accomplished by known methods. For example, the specific binding partner can be attached to a solid carrier by cross-linking, by covalent binding or by physical coupling. Examples of solid carriers used in the instant invention include polypropylene tubes, polystyrene microtiter plates and nylon beads. When the ligand to be detected is an antigen, preparation of the insoluble phase can be accomplished by simply coating the tubes or plates with the appropriate antibody. When nylon beads are used, the appropriate antibody may be coalently coupled to the beads by the method of Faulstich et al. described in *FEBS Letters*, 48:226 (1974).

Liquids in which the presence and quantity of a ligand of interest can be determined may be naturally-occurring or synthetic. In many cases, the liquid will be a biological fluid, such as serum, plasma, whole blood, urine, amniotic fluid and cerebrospinal fluid. Ligands may also be determined by dissolving or dispersing the ligand in an appropriate non-aqueous liquid.

Determination of fluorescence polarization is carried out using known techniques and standard equipment. See, for example, Freifelder, D., Fluorescence Spectroscopy, *In: Physical Biochemistry* (2d ed.), 537–572, W. H. Freemant & Co. (1982).

The present invention will now be illustrated by the following examples, which are not to be considered limiting in any way.

EXAMPLE 1 HOMOGENEOUS FLUORESCENCE POLARIZATION IMMUNOASSAY

The following materials were obtained from Sigma Chemical Co.: avidin, N-hydroxysuccinimidobiotin, fluorescein isothiocyanate, and goat antirabbit IgG IgG, IgG fraction. Rabbit IgG fraction was obtained from Pel-Freez Biologicals. All solvents and buffers were of reagent grade quality. Biotin-fluorescein was synthesized as described above.

Synthesis of biotinylated rabbit IgG was carried out as follows: rabbit IgG (2 mg, 12.5 nmoles) was dissolved in 2 mls of pH=7.4 phosphate buffered saline. N-hydroxysuccinimidobiotin was dissolved in N,N-dimethylformamide and 0.3 mg (880 nmoles) of N-hydroxysuccinimidobiotin was added and incubated at room temperature for two hours. The biotinylation mixture was purified by chromotography on Sephadex G-25 (1×25 cm), using the same buffer as eluent resulting in separation of biotinylated antibody from free biotin. The biotin: antibody ratio was 16, as determined by measuring antibody concentration by absorbance at 280 nm and measuring biotin concentration by the method of Green, N. M., *Methods in Enzymology*, McCormack D. B. and L. B. Wright (ed.) 18A:418 (1970).

Polarization values were determined using an SLM fluorometer with xenon arc lamp, a monochrometer in the excitation beam set to 491 nm and a 10 nm bandwidth 520 nm filter in the emission beams. Polarization filters were placed in both excitation beams in order to make it possible to align the emission filter in parallel with or perpendicular to the excitation filter. An SLM SPC-822 data processing module was used in the photon counting mode to determine polarization values.

Antibody assay. To glass or plastic tubes or disposable cuvettes was added various amounts of goat anti-rabbit IgG IgG in an appropriate volume to obtain the final assay concentrations shown in FIG. 6. (All concentrations refer to final assay concentrations.) Biotin-antigen (rabbit IgG) was added to yield a final assay concentration of 60 ng/ml and the solution was incubated one hour at room temperature. Avidin was then added to a concentration of 80 ng/ml, followed after three minutes by sufficient biotin-fluorescein to yield a concentration of $1 \times 10^{-9}$M. Polarization was then measured. All materials were made up in 0.1 M phosphate-buffered saline. Antibody sample may approach the total volume of the assay as all other components may be added in very small volumes. The concentration of the other components was determined as follows.

Biotin-antigen concentration was determined by adding various concentrations (creating the concentrations shown in FIG. 5) of biotin-antigen to sufficient avidin to obtain a final concentration of 80 ng/ml. This combination was incubated for three minutes. Biotin-fluorescein (final concentration $1 \times 10^{-9}$ M) was added and polarization was determined. The level of biotin-antigen yielding 20% of maximum polarization change was chosen for the antibody and antigen assays.

Figure 4:
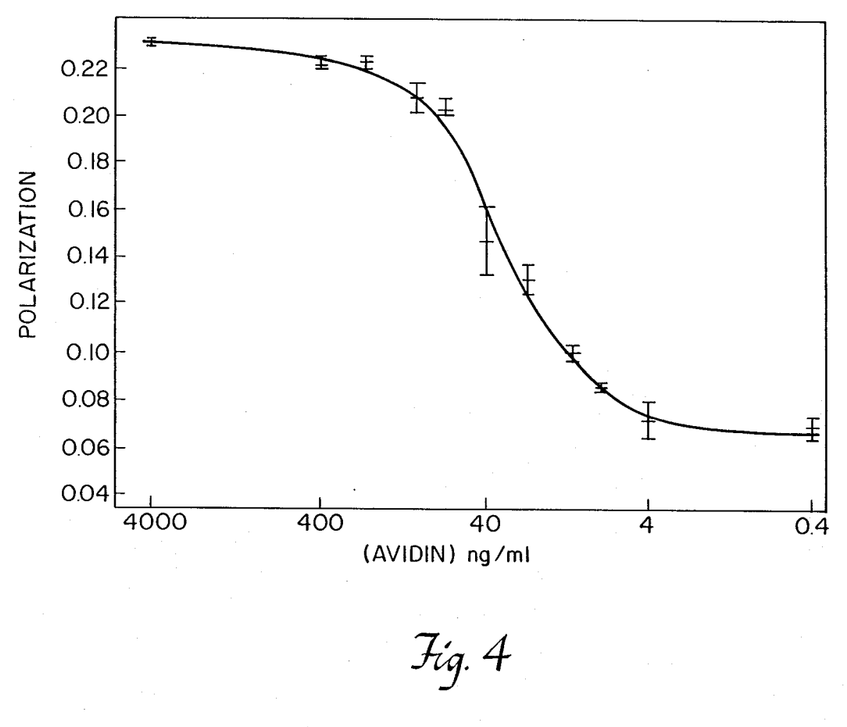
FIG. 4 is a schematic representation of the effect of avidin on the polarization of biotinfluorescein. Biotin-fluorescein concentration is $1 \times 10^{-9}$ M in 0.1M phosphate buffered saline (pH=7.4). Error bars represent the high, low, and average of triplicates.

The avidin concentration was chosen by selecting the level that yielded 80% of maximum polarization change when the effect of varying concentration of avidin on the polarization of biotin-fluorescein was determined (FIG. 4).

The biotin-fluorescein concentration was chosen to yield a 20:1 sample:buffer fluorescence ratio with no special precautions to reduce buffer fluorescence.

Antigen assay. Various amounts of antigen, rabbit IgG, yielding the concentrations shown in FIG. 7 were incubated one hour with goat antirabbit IgG IgG (4.4 ug/ml final concentration). The latter was chosen to obtain 60% of the maximum polarization change. Using the above concentrations, biotin-antigen was then added and incubated for one hour. Avidin was added and after three minutes, biotin-fluorescein was added and the polarization determined.

Incubation times of one hour (antigen with antibody) may be reduced to several minutes.

This assay may also be carried out with the immunological components bound to an appropriate solid phase. This requires longer reaction times, to allow for diffusion to the surface, but may yield improved sensitivity or a means of removing interfering sample substances.

The assay presented is a homogeneous fluorescence polarization immunoassay applicable to molecules regardless of their molecular weight. The strategy for this assay is outlined in Scheme 1. The assay is useful for detecting and quantifying antigens or antibodies. It is also applicable to any binding protein and its receptor as well as small molecules and their (large or small) binding agents.

Scheme 1

| Reaction | Variable | Constant | Products | Polarization |
|---|---|---|---|---|
| Fluorophore only | — | B-F | — | low |
| 1. (FIG. 1) | avidin | B-F | B-F-avidin | high |
| 2. (FIG. 2) | B-Ag | + avidin B-F | B-F avidin-B-A | low |
| 3. (FIG. 3) | Ab | + B-Ag avidin B-F | B-F-avidin B-Ag-Ab | high |
| 4. (FIG. 4) | Ag | + Ab B-Ag avidin B-F | B-F Ag-Ab avidin-B-Ag | low |

Abbreviations:
B-F = biotin-fluorescein
B-Ag = biotin-rabbit IgG
Ab = goat anti-rabbit IgG IgG
Ag = rabbit IgG The assay probe (B-F) is biotin covalently coupled to a fluorophore, which in this case is fluorescein. When excited by polarized light, B-F emits light which is depolarized (polarization is low) because of the rapid tumbling of this small molecule. When complexed to the more slowly tumbling macromolecule avidin, polarization is high (reaction 1.). Complexing of biotin and fluorescein is modulated by other components. Biotin is covalently coupled to one component (i.e., an antigen) of a complex-forming pair which consists of a ligand (i.e., the antigen) and a specific binding partner for the antigen (i.e., an antibody). The biotin-antigen is added in a concentration sufficient to complex with the avidin, allowing B-F to remain uncomplexed (reaction 2). If antibody is added initially, antibody complexes biotin-antigen and by steric blocking prevents avidin from binding biotin-antigen. This makes it possible for avidin to complex B-F resulting in high polarization (reaction 3.). When free antigen is added initially, antigen complexes antibody, which makes it possible for biotin-antigen to complex avidin. This results in free B-F and low polarization.

Thus the assay for antibody consists of reaction 3 and the assay for antigen is reaction 4. The change in polarization that occurs in each sequential reaction occurs in a manner dependent on the concentration of the variable reagent, as shown in the figures.

The effect of varying avidin (reaction 1) on the polarization of B-F is shown in FIG. 4. The polarization varies from 0.06 to 0.23 in this example; more highly purified samples of biotinluoroscein show a polarization change from 0.02-0.31. A concentration of $1 \times 10^{-9}$ M avidin was chosen for use in the following reactions.

Figure 5:
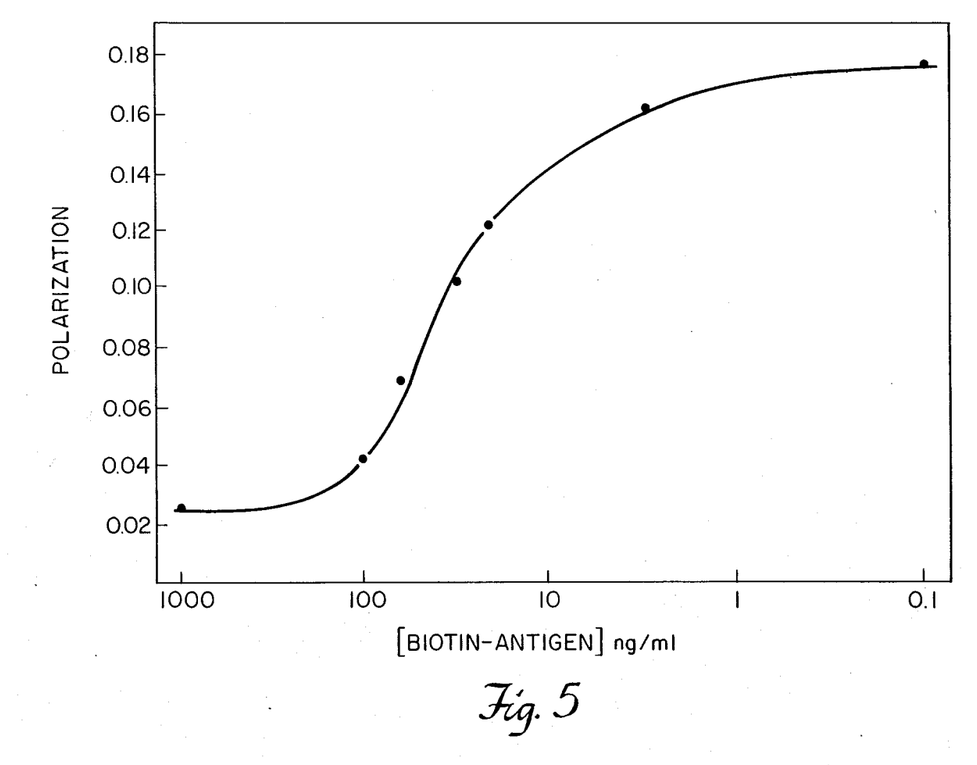
FIG. 5 is a schematic representation of the effect of biotin-antigen, in the presence of 80 ng/ml avidin, on the polarization of biotin-fluorescein as in FIG. 4. Data points are single determinations.

The effect of varying biotin-antigen (reaction 2) added initially followed by avidin and B-F on the polarization is shown in FIG. 5. A $1.5 \times 10^{-9}$ M concentration (based on protein) of biotin-antigen was chosen for use in reactions 3 and 4.

Figure 6:
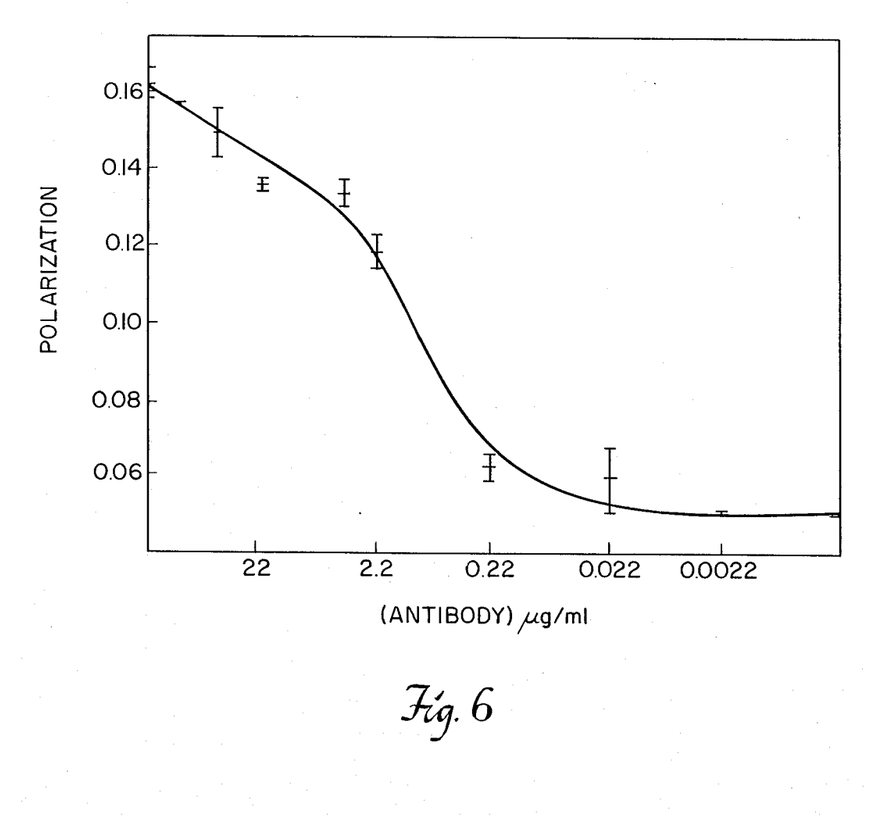
FIG. 6 is a schematic representation of the effect of anti-rabbit IgG, in the presence of 60 ng/ml biotin-rabbit IgG and 80 ng/ml avidin, added sequentially, on the polarization of biotin-fluorescein as in FIG. 4. Error bars are the high, low, and average of two different day runs normalized to the same initial polarization with zero antibody controls.

A standard curve for the assay of antibody (reaction 3) is represented in FIG. 6. Varying concentrations of antibody were added to the above biotin-antigen and incubated for one hour. Avidin and B-F were added and polarization measured. A typical competitive binding curve can be constructed from the data. Shorter incubation times may be used. This is IgG fraction polyclonal antibody and requires a higher concentration of antibody than biotin-antigen to neutralize the latter. This is due at least in part to its lack of purity, but may also indicate a requirement for more than a one-to-one complex to prevent access by avidin to the biotin. The assay range lies between about 0.2 and 20 ug/ml for this impure fraction. A concentration of $3 \times 10^{-8}$ M (4.4 ug/ml) was chosen for use in the following antigen assay.

Figure 7:
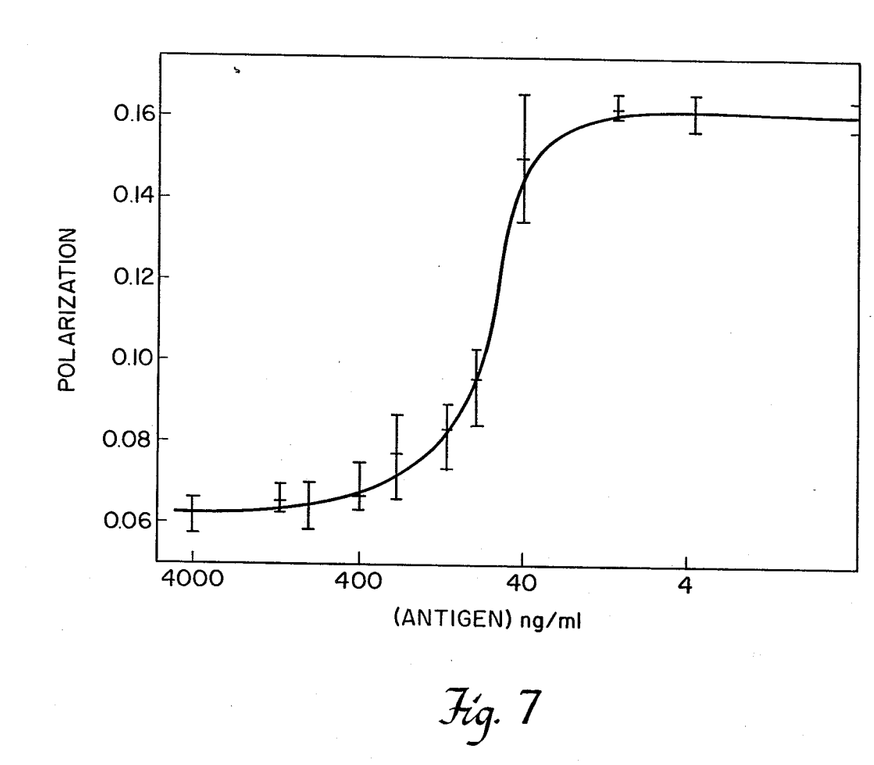
FIG. 7 represents the effect of rabbit IgG, in the presence of 4.4 ug/ml anti-rabbit IgG, 60 ng/ml biotin-rabbit IgG, and 80 ng/ml avidin, added sequentially, on the polarization of biotin-fluoroscein as in FIG. 4. Error bars are the high, low, and average of three same day runs normalized to the same initial polarization with zero rabbit IgG controls.

A standard curve for the assay of antigen (reaction 4) is shown in FIG. 7. The assay range is about 40 to 400 ng/ml ($2 \times 10^{-10}$ to $2 \times 10^{-9}$ M). The lower quantities of antigen required to neutralize the antibody is consistent with both explanations (see rationales above) for the amount of antibody required. The near equivalence of avidin and antigen levels required is remarkable and shows that there is no significant loss of sensitivity through the several steps in the procedure.

EXAMPLE 2 HETEROGENEOUS FLUORESCENCE POLARIZATION IMMUNOASSAY

Figure 8:
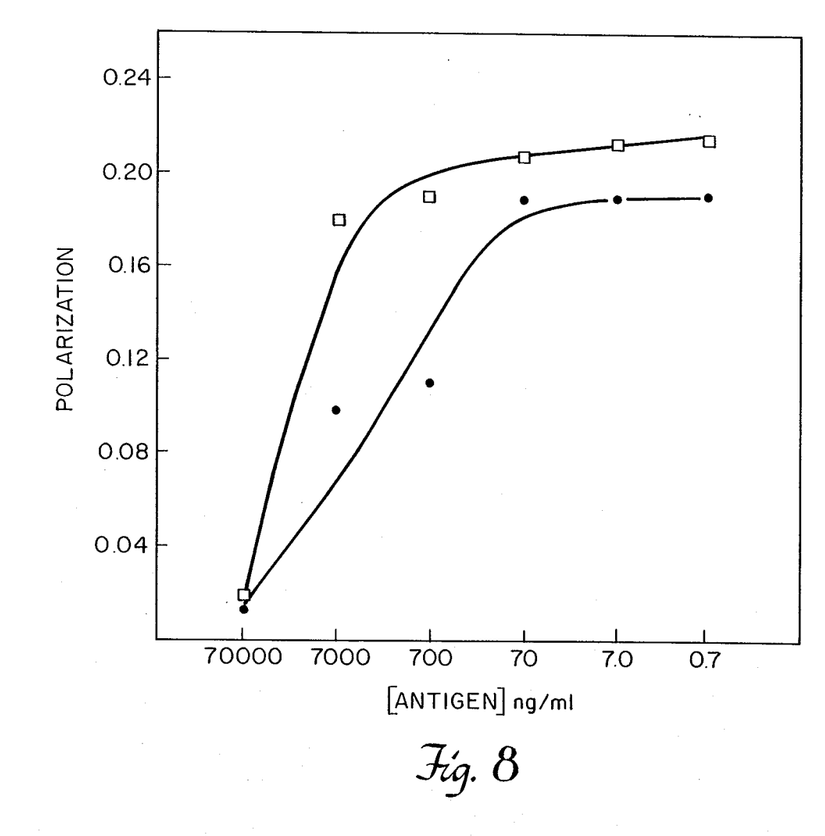
FIG. 8 is a schematic representation of the effect of rabbit IgG in the solid phase assay using polystyrene tubes coated with goat anti-rabbit IgG. The black squares represent 42 ng/ml. antigen-biotin; the black circles represent 84 ng/ml. antigen-biotin.

Polystyrene test tubes were coated with one ml. of a solution of affinity purified goat anti-rabbit IgG at 20 ug/ml 0.005 M phosphate buffered saline (PBS) (pH 7.4) for three days. The tubes were rinsed twice with 0.05 M PBS (pH 7.4) and filled with 900 ul 0.05 M PBS (pH 7.4). Serial dilutions of antigen yielding final concentrations shown in FIG. 8 were prepared in 0.12% Triton X-100 PBS; 100 ul aliquots were incubated in antibody-coating tubes for 2.5 hours at 37° C.

Antigen-biotin was added in 50 ul 0.12% Triton ™ X-100 PBS to yield a final concentration of 84 or 42 ng/ml. The tubes were incubated overnight at 37° C. Avidin was then added in 50 ul PBS to give a final concentration of 69 ng/ml followed by fluoroscein-biotin at a final concentration comparable to that in the homogeneous assay (see Example 1). The fluorescence polarization was then determined.

EXAMPLE 3 SIMULTANEOUS ASSAY

An alternative approach to this methodology has also been shown to be effective and to result in simplification of the assay in terms of the number of components in the antigen assay and the number of additions required. This involves a prior combination of components, rather than a sequential one and the elimination of the biotinylated antigen. Though an apparently minor variation in protocol, this changes the basis of the assay. The sequential assays above rely on a competition for avidin between biotin-fluorophore and biotin-antigen. This is modulated by antibody, which sterically prevents the large molecule avidin from binding the biotinantigen. In the simultaneous assay, an avidin: biotinylated antibody complex is performed. The addition of analyte (antigen) results in formation of larger complexes which sterically prevent small biotin-fluorophore from having access to the avidin. Biotin-fluorophore and avidin, therefore, do not bind. Similar simultaneous assays for antibody using a performed avidin: biotinylated-antigen complex can be performed.

Figure 9:
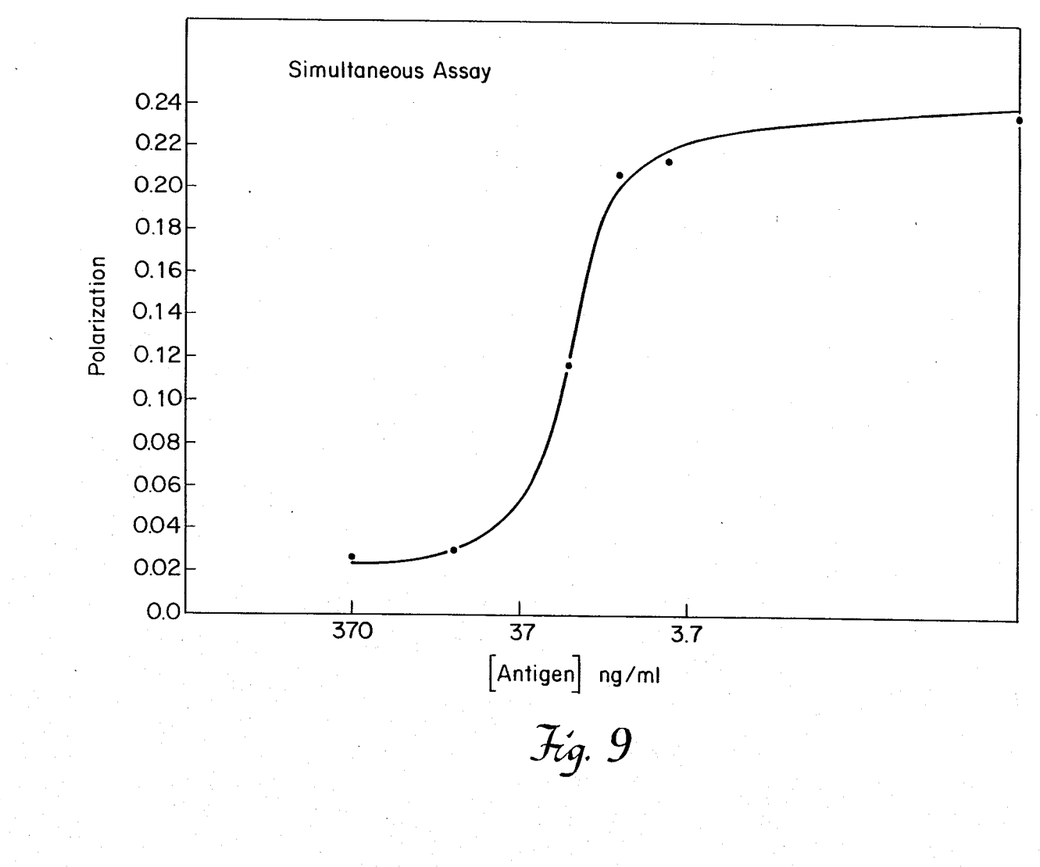
FIG. 9 represents the effect of rabbit IgG in the presence of avidin:biotin-anti-rabbit IgG on the polarization of biotin-fluoroscein.

In this method, avidin is mixed with biotinylated antibody in a 10:1 avidin:biotin-antibody ratio (this may be varied). This serves as a reagent. This complex is used at a concentration such that avidin is in site molar equivalence to the biotin-fluorophore concentration to be used in the assay. Varying concentrations of analyte antigen are incubated for short times with the avidin:biotin-antibody complex, biotin-fluorophore is added, and the polarization determined. Results are shown in FIG. 9, which represents the effect of rabbit IgG in the presence of avidin:biotin-anti-rabbit IgG on the polarization of biotin-fluorescein.

EQUIVALENTS

Those skilled in the art will recognize or be able to ascertain, using no more than routine experimentation, many equivalents to the specific embodiments of the invention described herein. Such equivalents are intended to be encompassed within the scope of this invention.

I claim:

1. A method of determining a ligand of interest in a liquid, comprising: incubating the liquid, biotin-labeled ligand of interest, biotin-labeled fluorophore, specific binding partner for the ligand of interest and avidin, under conditions appropriate for binding of ligand of interest and its specific binding partner to occur; measuring fluoroescence polarization of the liquid after incubation; and comparing the fluoroescence polarization measured with the fluoroescence polarization of a standard assayed identically as said liquid, wherein said standard contains a known quantity of the ligand of interest.

2. A method of claim 1 wherein the biotin-labeled fluorophore is biotin-labeled fluorescein.

3. A method of claim 1 wherein the ligand of interest is an antigen and the specific binding partner is an antibody specific for said antigen.

4. A method of claim 1 wherein the ligand of interest is an antibody and the specific binding partner is an antigen for which the antibody is specific.

5. A method of determining a ligand of interest in a liquid, comprising: incubating the liquid, biotin-labeled ligand of interest, biotin-labeled fluorophore, specific binding partner for the ligand of interest and avidin, under conditions appropriate for binding of ligand of interest and its specific binding partner to occur, and comparing fluorescence polarization after incubation with fluoroescence polarization of an avidin-free control, the control comprising the liquid, biotin-labeled ligand of interest and biotin-labeled fluorophore, wherein the difference between the fluorescence polarization after incubation and the fluorescence polarization of the avidin-free control is indicative of the amount of said ligand of interest in the liquid.

6. A method of determining a ligand of interest in a liquid, comprising the steps of:
   a. combining a volume of a liquid to be analyzed for the ligand of interest; biotin-labeled ligand of interest; biotin-labeled fluorophore; and specific binding partner for the ligand of interest, under conditions appropriate for specific binding reactions to occur between ligand of interest and its specific binding partner;
   b. measuring fluorescence polarization of the resulting combination;
   c. adding avidin to the resulting combination, under conditions appropriate for binding of avidin and biotin;
   d. measuring fluorescence polarization of the liquid; and
   e. determining the difference between fluorescence polarization measured in step (b) and fluorescence polarization measured in step (d), the difference in fluorescence being indicative of the amount of the ligand of interest.

7. A method of claim 6 wherein the ligand of interest is an antigen and the specific binding partner is an antibody specific for the antigen.

8. A method of claim 6 wherein the biotin-labeled fluorophore is biotin-labeled fluorescein.

9. A method of determining a ligand of interest in a liquid, comprising incubating (1) a volume of the liquid; (2) a complex comprised of biotin-labeled ligand of interest bound to a specific binding partner for said ligand of interest; and (3) avidin, under conditions appropriate for binding of ligand of interest and its specific binding partner to occur; adding biotin-labeled fluorophore; and determining fluorescence polarization of the liquid wherein the difference between the fluorescence polarization after incubation and the fluorescence polarization of an avidin-free control is indicative of the amount of said ligand of interest in the liquid.

10. A method of determining a ligand of interest in a liquid, comprising combining a volume of the liquid; a complex comprised of biotin-labeled ligand of interest bound to avidin; specific binding partner for said ligand of interest; and incubating the combination with biotin-labeled fluorophore, under conditions appropriate for binding of ligand of interest and its specific binding partner to occur, and subtracting the fluorescence polarization of the liquid, the complex and specific binding partner before incubation from the fluoroescence polarization of the liquid, the complex, specific binding partner and biotin-labeled fluorophore after incubation to attain a background corrected value, and comparing the corrected value to the fluorescence polarization of an avidin-free control comprising the liquid, biotin-labeled fluorophore, and specific binding partner for said ligand of interest, wherein the change in polarization is indicative of the amount of said ligand of interest.

11. A method of determining a ligand of interest in a liquid, comprising:
   a. incubating an insoluble phase containing a specific binding partner for the ligand of interest, the liquid, and biotin-labeled ligand;
   b. separating the insoluble phase from the soluble phase after incubation;
   c. incubating the soluble phase with biotin-labeled fluorophore;

d. measuring fluorescence polarization of the soluble phase;

e. incubating the soluble phase with a known quantity of avidin; and f. determining the change in fluorescence polarization of the soluble phase wherein the difference in the fluorescence polarization is indicative of the amount of said ligand of interest in the liquid.

12. A method of claim 11 wherein the ligand of interest in an antigen, the specific binding partner is an antibody specific for the antigen and the biotin-labeled fluorophore is biotin-labeled fluoroscein.

13. A method of determining a ligand of interest in a liquid, the ligand of interest having at least two binding sites for its specific binding partner, comprising:

a. incubating an insoluble phase containing a specific binding partner for the ligand of interest, the liquid, and biotin-labeled specific binding partner, under conditions appropriate for binding of the ligand of interest and its specific binding partner;

b. separating the insoluble phase from the soluble phase;

c. adding biotin-labeled fluorophore to the soluble phase;

d. incubating an aliquot of the soluble phase containing biotin-labeled fluorophore with avidin; and e. measuring the fluorescence polarization of the aliquot after incubation, wherein the difference between the fluorescence polarization after incubation and the fluroescence polarization of an avidin-free control is indicative of the amount of said ligand of interest in the liquid.

14. A method of determining a ligand of interest in a liquid, comprising:

a. incubating an insoluble phase containing a specific binding partner for the ligand of interest, the ligand and biotin-labeled specific binding partner for the ligand of interest, under conditions appropriate for binding of the ligand of interest and its specific binding partner;

b. separating the insoluble phase from the soluble phase;

c. incubating avidin with the insoluble phase;

d. separating the insoluble phase from the soluble phase;

e. incubating the insoluble phase with biotin-labeled fluorophore or incubating the soluble phase with biotin-labeled fluorophore; and f. measuring the fluorescence polarization after incubation of step (e) wherein the difference between the fluorescence polarization after incubation and the fluorescence polarization of an avidin-free control is indicative of the amount of said ligand of interest in the liquid.

15. A method of claim 14 in which the ligand of interest is an antigen, the specific binding partner is an antibody specific for the antigen and the biotin-labeled fluorophore is biotin-labeled fluorescein.

16. A method of determining a ligand of interest in a liquid, comprising:

a. incubating a volume of the liquid with (1) a complex comprised of avidin and biotin-labeled specific binding partner for the ligand of interest; and (2) biotin-labeled fluorophore, under conditions appropriate for binding reactions to occur between ligand of interest and its specific binding partner;

b. measuring fluorescence polarization after incubation; and c. comparing the measured fluorescence polarization with fluorescence polarization of a control, the control comprising the liquid, biotin-labeled binding partner and biotin-labeled fluorophore wherein the difference in fluorescence polarization is indicative of the amount of said ligand of interest in the liquid.

17. A method of determining an antibody in a liquid, comprising:

a. incubating a volume of the liquid; biotin-labeled antigen for which the antibody is specific; avidin and biotin-labeled fluorophore;

b. measuring fluorescence polarization after incubation; and c. comparing the measurement made after incubation with fluorescence polarization of an avidin-free control, wherein the difference between the fluorescence polarization of the liquid after incubation and the fluorescence polarization of the avidin-free control is indicative of the amount of said ligand of interest in the liquid.

18. A method of determining a ligand of interest in a liquid, the ligand of interest having at least two binding sites for its specific binding partner, comprising:

a. incubating an insoluble phase containing a specific binding partner for the ligand of interest, the liquid, and biotin-labeled specific binding partner, under conditions appropriate for binding of the ligand of interest and its specific binding partner;

b. separating the insoluble phase from the soluble phase;

c. adding avidin to the insoluble phase;

d. measuring fluorescence polarization of the product of (c);

e. separating the insoluble phase from the soluble phase;

f. incubating the insoluble phase with biotin-labeled fluorophore;

g. measuring the fluorescence polarization of the insoluble phase of (f);

h. subtracting measurement (d) from measurement (g); and i. comparing the resultant value of (h) to the fluorescence polarization of an avidin-free control subjected to method steps (a), (b), (f) and (g) wherein the change in fluorescence polarization is indicative of the amount of said ligand of interest in the liquid.

* * * * *